United States Patent
Jensen

(10) Patent No.: US 7,297,158 B2
(45) Date of Patent: Nov. 20, 2007

(54) MULTILAYER COMPOSITE VASCULAR ACCESS GRAFT

(75) Inventor: Bjorn Jensen, Livermore, CA (US)

(73) Assignee: Thoratec Corporation, Livermore, CA (US)

( * ) Notice: Subject to any disclaimer, the term of this patent is extended or adjusted under 35 U.S.C. 154(b) by 109 days.

(21) Appl. No.: 10/868,023

(22) Filed: Jun. 14, 2004

(65) Prior Publication Data

US 2005/0278018 A1 Dec. 15, 2005

(51) Int. Cl.
*A61F 2/06* (2006.01)

(52) U.S. Cl. ...................... 623/1.44; 623/1.4

(58) Field of Classification Search ....... 623/1.35–1.49
See application file for complete search history.

(56) References Cited

U.S. PATENT DOCUMENTS

| | | | |
|---|---|---|---|
| 4,409,172 A | 10/1983 | Ward, Jr. et al. | 264/209.2 |
| 4,604,762 A | 8/1986 | Robinson | 623/1 |
| 4,731,073 A | 3/1988 | Robinson | 623/1 |
| 4,955,899 A | 9/1990 | Della Corna et al. | 623/1 |
| 5,104,400 A | 4/1992 | Berguer et al. | 264/132 |
| 5,152,782 A | 10/1992 | Kowligi et al. | 623/1 |
| 5,192,310 A | 3/1993 | Herweck et al. | |
| 5,628,782 A * | 5/1997 | Myers et al. | 623/2.25 |
| 5,910,168 A | 6/1999 | Myers et al. | |
| 6,428,571 B1 * | 8/2002 | Lentz et al. | 623/1.4 |
| 6,939,377 B2 * | 9/2005 | Jayaraman et al. | 623/1.46 |

FOREIGN PATENT DOCUMENTS

WO    WO 98/26731    6/1998

OTHER PUBLICATIONS

International Search Report for PCT/US2005/015297, filed Apr. 29, 2005, mailed Feb. 26, 2007, 10 pgs.

* cited by examiner

*Primary Examiner*—Suzette Gherbi
(74) *Attorney, Agent, or Firm*—Squire, Sanders & Dempsey LLP

(57) ABSTRACT

A multilayer composite vascular access graft and a method of constructing such a graft are disclosed. The mcVAG has improved performance characteristics, which include desirable handling characteristics such as ease of suturing, kink resistance and the ability to serve as a cannulation route soon after the implant procedure.

19 Claims, 4 Drawing Sheets

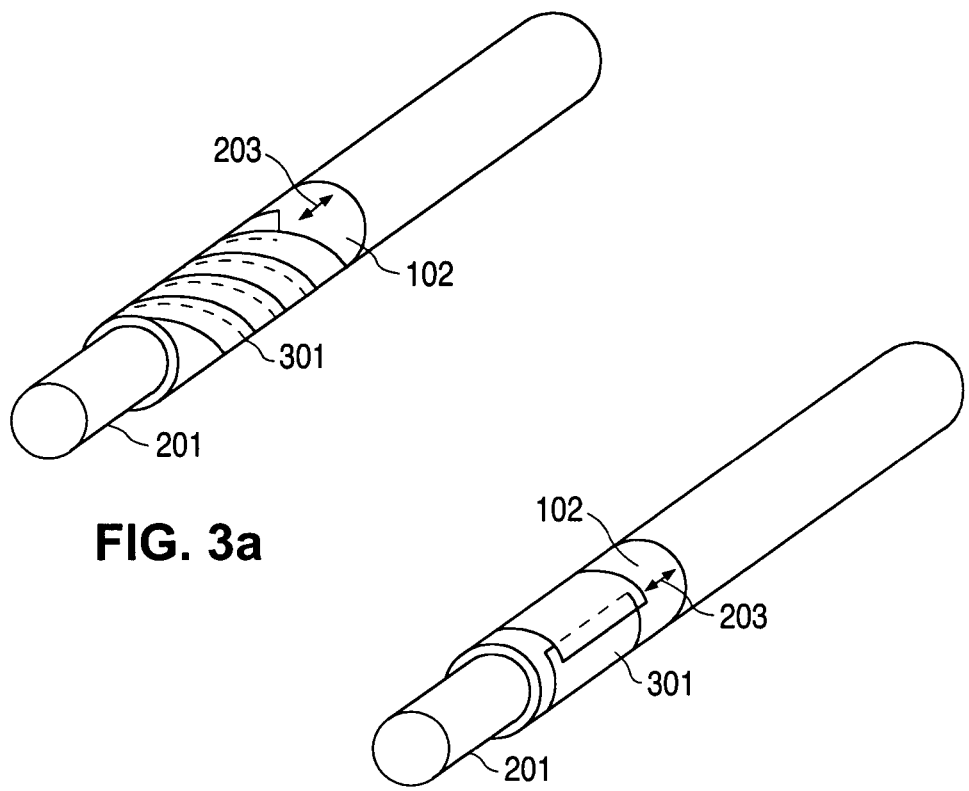
FIG. 3a
FIG. 3b
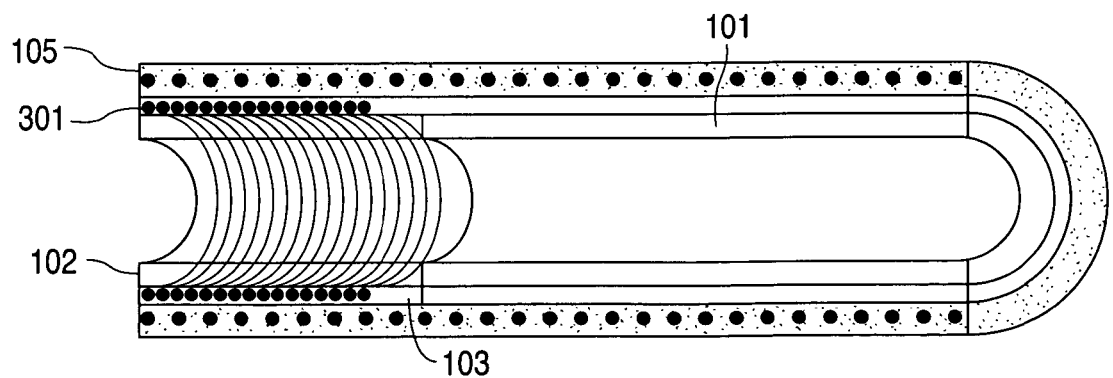
FIG. 4

MULTILAYER COMPOSITE VASCULAR ACCESS GRAFT

BACKGROUND

1. Field of the Invention

This invention relates to prosthetic vascular access grafts. More particularly, this invention relates to multilayer composite vascular access grafts and their method of construction.

2. Description of the State of the Art

Vascular access is the method used to access the bloodstream for hemodialysis patients. Hemodialysis removes blood from the body and routes it to an artificial kidney machine where the blood is cleansed and returned to the patient. Hemodialysis patients require easy and routine access to the bloodstream. The most common forms of vascular access are an arteriovenous (A/V) fistula, a central venous catheter (CVC) for temporary access and a prosthetic vascular access graft (VAG). The A/V fistula generally takes 1 to 4 months after surgery to develop, and a CVC is generally inserted until the fistula is ready for use. A VAG is a synthetic tube that is implanted under the skin in your arm and connected to an artery and a vein. The VAG is the most widely used vascular access device for long term vascular access in the hemodialysis patient, since there are a variety of factors that prevent the use of an A/V fistula. More than 60% of the hemodialysis patients in the United States have a VAG.

Hemodialysis patients have benefited from high-flow cannulation VAGs for decades. A primary material used in the construction of a VAG is expanded polytetrafluoroethylene (ePTFE). The ePTFE graft has become a standard among vascular surgeons due to its high kink-resistance, conformability and biocompatibility. The primary disadvantage of the ePTFE graft is that it must be allowed to "mature" for at least two weeks after the implant procedure to ensure that sufficient tissue in-growth has occurred and, although not necessarily required, it is often hoped that cell endothelialization has occurred as well. This maturation time helps to provide hemostasis, long-term healing ability and patency to the graft.

Polyurethane VAGs have been introduced into the U.S. marketplace over the past three years and are beneficial in that they are available for cannulation immediately after implant, are self-sealing, and as a result, provide rapid post-cannulation hemostasis. There are a number of disadvantages with these grafts including undesired handling characteristics that make it difficult for the surgeon to create an anastomosis, particularly with smaller blood vessels. In addition, the high elasticity of polyurethane can result in pulling and kinking in the region of the anastomosis. Accordingly, one of skill in the art in the field of VAGs would benefit from the introduction of a VAG with improved performance characteristics, which include handling characteristics such as ease of suturing, kink resistance and the ability to serve as a cannulation route soon after the implant procedure.

SUMMARY

Multilayer composite vascular access grafts and their methods of manufacture are provided. In one embodiment, the multilayer composite vascular access graft comprises a first layer, a second layer in contact with or positioned at a distance from the first layer to form a horizontally aligned composite layer, and a conjoining layer disposed on the composite layer to conjoin the first layer to the second layer. The multilayer composite vascular access graft can further comprise a fiber-reinforced layer disposed on the conjoining layer. In another embodiment, the multilayer composite vascular access graft comprises a first layer, a second layer and a fiber-reinforced layer. The second layer is deposited on the first layer, and the second layer is coated with a fiber-reinforced layer.

The multilayer composite vascular access graft (mcVAG) has improved performance characteristics, which include desirable handling characteristics such as ease of suturing, kink resistance and the ability to serve as a cannulation route soon after the implant procedure.

BRIEF DESCRIPTION OF THE DRAWINGS

FIGS. 3a and 3b illustrate alternate methods of applying a mask using a wrapping tape according to embodiments of the present invention.

FIG. 4 illustrates a cross-section of a mcVAG and an alternate method of applying a mask using a wrapping fiber according to one embodiment of the present invention.

DETAILED DESCRIPTION

As discussed in more detail below, the invention generally includes a multilayer composite vascular access graft (mcVAG) and a method of constructing such a graft. The mcVAG includes a combination of materials that differ in their physical characteristics. The resulting vascular access graft has improved performance characteristics, which include desirable handling characteristics such as ease of suturing, kink resistance and the ability to serve as a cannulation route soon after the implant procedure.

Figure 1:
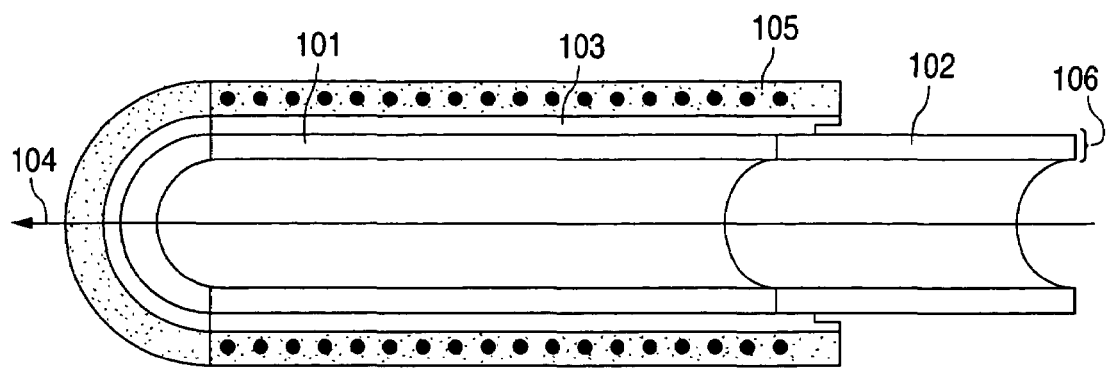
FIG. 1 illustrates a cross-section of a multilayer composite vascular access graft (mcVAG) with a conjoined, composite inner layer according to one embodiment of the present invention.

FIG. 1 illustrates a cross-section of a mcVAG with a conjoined, composite inner layer according to one embodiment of the present invention. In this embodiment, the mcVAG can be constructed according to any desired dimension and conformation and comprises a first inner layer component 101; a second inner layer component 102; a conjoining layer 103; an inner lumen 104; and, an optional fiber-reinforced layer 105. The first and second inner layer components 101 and 102 form what will be referred to as "a composite inner layer," which may comprise any combination of components 101 and 102 and can be arranged in any order. The term "composite inner layer 102, 101, 102" will be used to refer to any variation of these components in a composite inner layer, including, for example, (i) a mcVAG with a composite inner layer 102, 101, which would have a first inner layer component 101 and a second inner layer component 102 at only one end of the mcVAG; and, (ii) a mcVAG with a composite inner layer 102, 101, 102, which would have a first inner layer component 101 and a second inner layer component 102 at each end of the mcVAG.

The structural dimensions of the mcVAG can vary within the range of dimensions known to be useful to one of skill in the art. In some embodiments, the inner layer components 101 and 102, conjoining layer 103 and optional fiber-reinforced layer 105 can be uniform in thickness or variable in thickness throughout the layer. In other embodiments, a wall thickness 106 for first inner layer component 101 and the second inner layer component 102 can range from about 0.1 millimeter to about 1.0 millimeter, or any range therein. In another embodiment, the inner lumen 104 can have an inner diameter ranging from about 1.0 millimeter to about 30 millimeters, or any range therein. In one example, the inner lumen 104 can have an inner diameter ranging from about 5.0 millimeters to about 6.0 millimeters. In another embodiment, the length of the composite inner layer 102, 101, 102 can range from about 1.0 centimeters to about 100 centimeters, or any range therein. In one example, the length of the composite inner layer 102, 101, 102 can range from about 20 centimeters to about 50 centimeters. In another embodiment, there is a second inner layer component 102 at each end of the mcVAG, and the lengths of the second inner layer components are not equal.

It should be appreciated that the mcVAG can be comprised of any number of layers and that each layer of the mcVAG can be formed by any method known to one of skill in the art. Each layer of the present invention can be either porous or non-porous. In one embodiment, the composite inner layer 102, 101, 102 can be porous and the conjoining layer 103 can be non-porous. In another embodiment, the composite inner layer 102, 101, 102 can be porous; the conjoining layer 103 can be non-porous; and, the fiber-reinforced layer 105 can be porous. In another embodiment, the composite inner layer 102, 101, 102 can be porous; the conjoining layer 103 can be non-porous; and, the fiber-reinforced layer 105 can be non-porous. In some embodiments, the layers are formed by coating or extrusion. Any method of coating can be used in practicing the present invention including, but not limited to, spraying, dipping, brushing, pouring, spinning, roller coating, meniscus coating, powder coating and various inking approaches such as inkjet-type application. In some embodiments, the method of coating is spraying. In other embodiments, the method of coating is dipping. A dipping method is taught in U.S. Pat. No. 4,409,172.

Casting solvents may be required in the formation of each layer of the mcVAG. A casting solvent can be a liquid medium within which a desired solid material can be solubilized for application. The casting solvent must be carefully selected to avoid adversely affecting an underlying material such as, for example, the underlying first inner layer 101 and second inner layer 102. An underlying material should not be adversely affected where it is reasonably insoluble in a casting solvent used to apply an overlying layer. For purposes of the present invention, a material is reasonably insoluble in a casting solvent when, despite some solubility of the material in the solvent during casting, the product can still be used for its intended purpose. It should be appreciated, however, that the contact between layers can include an integration of an overlying layer with the underlying layer. The integration involves a reduction or elimination of the line of demarcation between layers without adversely affecting either layer. Casting solvents can be selected to achieve an integration of layers.

The casting solvent may be chosen based on several criteria including, for example, its polarity, molecular weight, biocompatibility, reactivity and purity. Other physical characteristics of the casting solvent may also be taken into account, including the solubility limit of the conjoining layer 103 in the casting solvent; oxygen and other gases in the casting solvent; the viscosity and vapor pressure of the combined casting solvent and conjoining layer 103; the ability of the casting solvent to diffuse through an underlying material; and the thermal stability of the casting solvent. One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. It should be appreciated that the curing process may affect the chemical structure of the underlying materials and, thus, their solubility in the casting solvent. It should also be appreciated that the kinetics of dissolution are also a factor to consider when selecting the casting solvent, because a slow dissolution of a material may not affect the performance characteristics of a product due to a relatively fast processing time. Exemplary casting solvents for use in the present invention include, but are not limited to, dimethyl acetamide (DMAC) and tetrahydrofuran (THF).

In one example, the materials used to form the first inner layer component 101 and the second inner layer component 102 may both be soluble in a highly polar casting solvent such as, for example, water, but may be reasonably insoluble in a lower polarity casting solvent such as, for example, butanol. In this example, a low polarity casting solvent can be used for depositing the conjoining layer 103 on the composite inner layer 102, 101, 102 without disrupting the structure of first inner layer component 101 or second inner layer component 102 to an extent great enough to prevent them from being used for their intended purpose of serving as a composite inner layer 102, 101, 102 within a mcVAG.

Each layer can be applied as liquid coating and dried to produce a solid coating. The drying process may be limited to drying without structural chemical changes in the material used to form the coating product, and it may also include curing. Regardless, the solid product is a relatively stable and inert material with all its performance properties intact. Some materials dry under ambient conditions without the aid of any additional process conditions. Other materials dry during treatment with steam or heating in an oven. Many polyester resins require a post-curing processes, which may include a heating-cooling cycle to increase the extent of the cure. Examples of process conditions used to properly dry a material include, but are not limited to, heat, electromagnetic radiation, electron beam, ion or charged particle beam, neutral-atom beam, chemical energy or a combination thereof. The electromagnetic radiation may include light and can be broadband or specific wavelengths. In one embodiment, the drying can occur under ambient conditions without additional application of heat, electromagnetic radiation, electron beam, ion or charged particle beam, neutral-atom beam, or chemical energy.

In one embodiment, the first inner layer component 101 can be formed by coating a mandrel 201 with a polymer or combination of polymers, in a form that is blended, mixed, bonded or connected. For example, polyurethane can be used to form a first inner layer component 101 in the shape of the mandrel 201. In another embodiment, the second inner layer component 102 can be formed, for example, using ePTFE and extrusion techniques that are well-known by one of skill in the art. Essentially, an extruded PTFE is expanded to form an ePTFE second inner layer component 102. Process parameters can be controlled to alter the characteristics of the ePTFE, and such process parameters include, but are not limited to, rate of expansion, deformation level, and temperature. These process parameters can be varied in order to control structural features such as, for example, the microporous structure of the ePTFE tube. Examples of microporous structural features that affect the performance characteristics of the mcVAG include, but are not limited to, fibril orientation and node size. Methods for creating ePTFE tubes with desired characteristics, including multilayer tubes, are taught in U.S. Pat. No. 6,428,571.

Figure 2A:
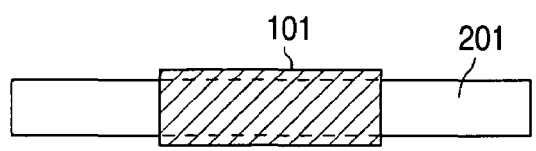
FIGS. 2a-2c illustrate a method of depositing a conjoining layer in the construction of a mcVAG with a conjoined, composite inner layer according to one embodiment of the present invention.
Figure 2B:
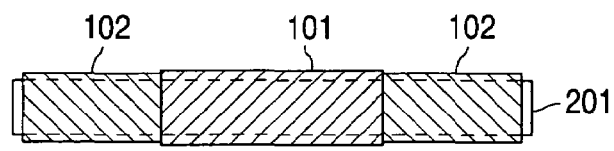
Figure 2C:
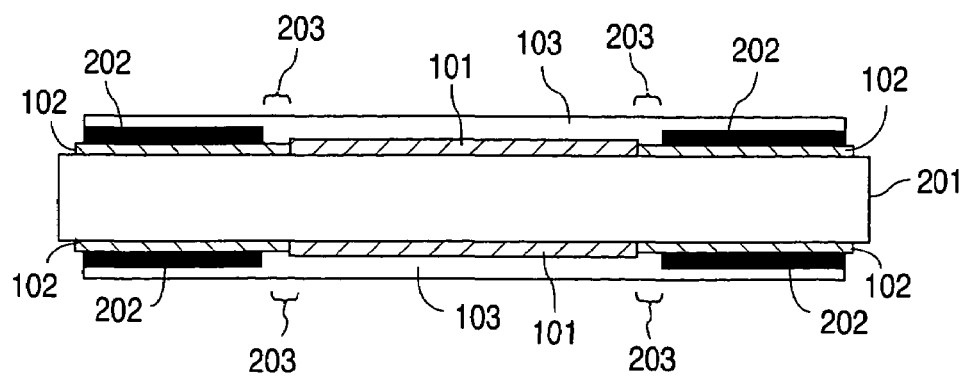

FIGS. 2a-2c illustrate a method of depositing a conjoining layer in the construction of a mcVAG with a conjoined, composite inner layer according to one embodiment of the present invention. In FIG. 2a, the first inner layer component 101 is formed on a mandrel 201 by dipping the mandrel 201 into a vat of first inner layer component 101, drying first inner layer component 101 and trimming first inner layer component 101 at both ends to produce clean edges. Examples of materials that may be used in the formation of the first inner layer component 101 include, but are not limited to, silicones; silicone rubbers; synthetic rubbers; polyethers; polyesters; polyolefins; modified polyolefins such as, for example, halogenated polyolefins that include, but are not limited to, fluorinated polyolefins; polyamides; fluorinated ethylene propylene copolymer (FEP); polyfluorinated alkanoate (PFA); polyurethanes; segmented-polyurethanes; segmented polyether-polyurethanes; polyurethaneurea; silicone-polyurethane copolymers; and, any analogs, homologues, congeners, derivatives, salts and combinations thereof. In one embodiment, the first inner layer component 101 can be comprised of polyurethane. In another embodiment, the first inner layer component 101 can be comprised of Thoralon® (Thoratec Corp.) The two major components in Thoralon® are surface modifying additives and BPS-215 polyurethaneurea, a high-flex-life elastomer. In any embodiment of the present invention, a salt of a polymer can be added for a variety of reasons such as, for example, to provide solubility, conductivity or reactivity.

It is to be appreciated that a mandrel may not be necessary in the construction of a mcVAG of the present invention. However, where a mandrel 201 is used, it should be comprised of materials that are not substantially altered by the chosen process variables such that the mandrel 201 can still be used for its intended purpose. Relevant process variables include, but are not limited to, choice of casting solvents and methods of drying. Furthermore, the mandrel 201 should not be comprised of a material that will adhere or bond to the first inner layer component 101 or second inner layer component 102. The mandrel 201 can be comprised of any material or a combination of materials known to one of skill in the art to be useful in the formation of polymeric layers. In one embodiment, the mandrel comprises stainless steel. In another embodiment, the mandrel comprises glass. In another embodiment, the mandrel comprises wax. The surface properties of the mandrel 201 can also be chemically or physically altered to produce a desired outcome such as, for example, a reduction in surface adhesion or formation of a textured surface on the inner lumen 104.

In FIG. 2b, the second inner layer components 102 are slipped onto both ends of the mandrel 201 until they communicate with the first inner layer component 101 to form a composite inner layer 102, 101, 102. Examples of materials that may be used in the formation of the second inner layer component 102 include, but are not limited to, silicones; silicone rubbers; synthetic rubbers; polyethers; polyesters; polyolefins; modified polyolefins such as, for example, halogenated polyolefins that include, but are not limited to, fluorinated polyolefins; polyamides; FEP; PFA; polyurethanes; segmented-polyurethanes; segmented polyether-polyurethanes; polyurethaneurea; silicone-polyurethane copolymers; and, any analogs, homologues, congeners, derivatives, salts and combinations thereof. In one embodiment, the second inner layer component 102 can be comprised of PTFE. In another embodiment, the second inner layer component 102 can be comprised of ePTFE. A common type of PTFE is Teflon® (DuPont, Inc.), and common types of ePTFE are Gore-Tex® (W.L. Gore and Assoc., Inc.) and SoftForm® (EZX Corp.). Both PTFE and ePTFE are biologically inert, non-biodegradable, typically softer than implants comprising silicone and can be manufactured in many forms including, but not limited to, sheets, strands and tubes. The ePTFE is well-suited for a vascular access graft because it is a woven mesh-like form of PTFE that is flexible, soft, strong and sufficiently porous to allow for integration of body tissue within the ePTFE structure. In another embodiment, there is only one second inner layer component 102. In another embodiment, there is a second inner layer component 102 at each end of the mcVAG, and the lengths of the second inner layer components are not equal.

The communicating between the first inner layer component 101 and the second inner layer component 102 includes, but is not limited to, abutting, overlapping or placing in close proximity. In the composite inner layer 102, 101, 102, the first inner layer component 101 communicates with the second inner layer components 102 such that the first inner layer component 101 and the second inner layer components 102 form an inner lumen 104 that is continuous.

The first inner layer component 101 and the second inner layer component 102 are preferably porous. While not intending to be bound by any theory or mechanism of action, the inner lumen 104 is a blood interface that can eventually develop a biologic lining composed of platelets, endothelial-like cells, macrophages and lymphocytes. As a result, the inner lumen 104 can comprise a biologic pseudointima that makes use of an anticoagulant typically unnecessary. Accordingly, the mcVAG can be designed such that the inner lumen 104 has a structure that promotes endothelialization to prevent or inhibit thrombus formation.

Endothelialization can be promoted by creating a porous or rough surface on the inner lumen 104. An average pore diameter sufficient to promote endothelialization can range from 1 micron to about 400 microns, from about 2 microns to about 200 microns, from about 4 microns to about 100 microns, from about 8 microns to about 80 microns, from about 10 microns to about 20 microns, or any range therein. In another embodiment, the inner lumen 104 has a rough surface comprising, for example, pits, grooves, flutes, fibrils, protuberances or a combination thereof. The intersections where fibrils meet are termed "nodes," and the distance between nodes is termed the "internodal distance." The internodal distance can range from about 40 microns to about 200 microns, from about 50 microns to about 100 microns, from about 60 microns to about 75 microns, or any range therein. In some embodiments, nodes are only present in the first inner layer component 101.

Porosity can be introduced into the layers of the present invention by any method known to one of skill in the art. In one embodiment, the porosity can be introduced into the layers by adding particles to the materials used to form the layers. For example, the first inner layer component 101 and second inner layer component 102 can be made porous by adding particles to the material, forming the layer, and then removing the particles to create porous structures. In some embodiments, the porous structure is present only in the first inner layer component 101. Pore size can be controlled by screening the particles according to size and adding particles of a predetermined size to the materials. The particles may include, but are not limited to, salts and water-soluble polymers. In some embodiments, water-soluble polymers include, for example, polymeric salts, polyvinyl alcohol, polyethylene glycol, polyethylene oxide, dextran, and combinations thereof. Such particles may be removed, for example, by washing in water or a very dilute acid bath. Examples of non-polymeric salts include, but are not limited to, NaCl and sodium bicarbonate (bicarb). In other embodiments, the methods of forming the porous structure include stretching the first inner layer component 101 and the second inner layer component 102 to induce formation of pores or voids in the material. In one example, the first inner layer component 101 and the second inner layer component 102 can be formed to a predetermined smaller size and stretched to a necessary dimension. In other embodiments, the methods of forming the porous structure include precipitation of a cast polymer solution in an aqueous liquid such as, for example, water, prior to curing. In other embodiments, the methods of forming the porous structure include pressuring and sintering a powder of a polymer such as, for example, PTFE to form a film with internal bridging that may be stretched to control the size of the pore structure created; and, bombardment of a polymer film with high-energy particles followed by chemical etching to create a pore structure.

In some embodiments, a layer is "porous" when it has a void-to-volume percentage that ranges from about 40% to about 90%, from about 70% to about 80%, or any range therein. In some embodiments, a layer is "non-porous" when it has a void-to-volume percentage that ranges from about 0% to about 5%, from about 1% to about 3%, and any range therein. The "void-to-volume percentage" is defined as the volume of the pores divided by the total volume of the layer including the volume of the pores. In some embodiments, the void-to-volume percentage can be measured using standard test method BSR/AAMI/ISO 7198, which has been adopted in-whole as a revision of ANSI/AAMI VP20-1994 (Cardiovascular Implants—Vascular Prosthesis section 8.2.1.2, Method for Gravimetric Determination of Porosity, Am. Nat'l Stds. Inst./Assoc. for the Adv. of Med. Instr.)

The layers of the mcVAG may also be at least partially coated with an antiplatelet, anticoagulant, antifibrin, antithrombin, or a combination thereof, to prevent or inhibit thrombus formation. Examples of antiplatelets, anticoagulants, antifibrins and antithrombins include, but are not limited to, albumin, gelatin, glycoproteins, heparin, hirudin, recombinant hirudin, argatroban, forskolin, vapiprost, prostacyclin, dextran, D-phe-pro-arg-chloromethylketone (synthetic antithrombin), dipyridamole, platelet receptor antagonist glycoprotein IIb/IIIa antibodies such as 7E-3B, thrombin inhibitors such as ANGIOMAX (Biogen, Inc.), and any analogs, homologues, congeners, derivatives, salts and combinations thereof.

In some embodiments, the inner lumen 104 can act as a scaffolding for host cells comprising nucleic acids encoding for polypeptides that are antithrombogenic. In another embodiment, the inner lumen 104 can be surface-modified with polyethylene glycol (PEG). For example, a PEG-diisocyanate with a molecular weight of about 3400 daltons may potentially react with protein amines to form molecular barriers on adsorbed proteins on inner lumen 104 to prevent or inhibit the attachment of adhesive ligands and formation of acute surface thrombosis. In other embodiments, surface treatments including, but not limited to, plasma treatment, corona discharge, flame treatment, thermal treatment, chromic acid etching, and sodium treatment may be used to control surface properties such as, for example, the surface tension or reactivity of a polymer surface and to potentially introduce functional groups such as, for example, hydroxyl, carbonyl, carboxyl, sulfoxyl, aldehyde, hydroperoxide, ether, ester, amino and amido groups.

In FIG. 2c, the conjoining layer 103 is deposited on a segment of the composite inner layer 102, 101, 102. A mask 202 is applied on the second inner layer components 102 such that portions 203 of the second inner layer components 102 are left unmasked in preparation for depositing the conjoining layer 103 on the composite inner layer 102, 101, 102. The conjoining layer 103 is then deposited on the masked composite inner layer 102, 101, 102 to conjoin the first inner layer component 101 to the second inner layer components 102 and form an inner lumen 104 that is continuous and sealed. In one embodiment, the portions 203 can range from about 0.05 inches to about 12 inches in length, from about 0.1 inches to about 6 inches in length, from about 0.2 inches to about 3 inches in length, from about 0.25 inches to about 0.75 inch in length, or any range therein.

The method used for depositing the conjoining layer 103 on the composite inner layer 102, 101, 102 depends on whether conjoining layer 103 was preformed prior to the depositing. As described above, the conjoining layer 103 can be preformed, for example, through an extrusion process or on a mandrel 201, or it can be applied directly as a liquid coating on the composite inner layer 103. In one embodiment, the conjoining layer 103 can be a preformed tubular material that is expanded and placed on a composite inner layer 102, 101, 102 on a mandrel 201. In another embodiment, the conjoining layer 103 can be a liquid that is sprayed on a composite inner layer 102, 101, 102 on a mandrel 201 and dried under ambient conditions. In another embodiment, the composite inner layer 102, 101, 102 can be dipped into a vat of liquid conjoining layer 103, and the conjoining layer 103 can be dried with any method described above.

The mask 202 should be comprised of a material that is reasonably insoluble in the casting solvent used to deposit the conjoining layer 103. In some embodiments, the mask 202 can be easily removed with a solvent that will not adversely affect other materials in the mcVAG. These embodiments may require the use of such a solvent, because the mask 202 can sometimes unavoidably adhere to the composite inner layer 102, 101, 102. For example, if the casting solvent used to deposit the conjoining layer 103 is DMAC, then the mask 202 should be reasonably insoluble in DMAC. Likewise, if the casting solvent is THF, then the mask 202 should be reasonably insoluble in THF. In one embodiment, the mask 202 can be a layer of salt that was applied to the composite inner layer 102, 101, 102 as a supersaturated solution. A variety of salts may be used as the mask 202 and removed with either water or a weak acid. In one example, the mask 202 comprises NaCl, which may be easily removed with water after depositing the conjoining layer 103 and is reasonably insoluble in a DMAC casting solvent. In another embodiment, the mask 202 can be made from a water-soluble polymer. In some embodiments, water-soluble polymers may include, for example, polymeric salts, polyvinyl alcohol, polyethylene glycol, polyethylene oxide, dextran, and combinations thereof. In another embodiment, the mask 202 can be made from a material that may not be easily removable by a solvent and, thus, requires removal by applying force without additional application of a solvent. Examples of such masks 202 include, but are not limited to, metals and metal alloys such as, for example, aluminum, stainless steel, gold, cured silicone, and the like.

FIGS. 3a and 3b illustrate alternate methods of applying a mask using a wrapping tape according to embodiments of the present invention. In FIG. 3a, a masking wrap 301 is applied as a wrapping tape around the second inner layer component 102 such that it overlaps tightly upon itself in order to avoid penetration of the masking wrap 301 by the conjoining layer 103. In FIG. 3b, a masking wrap 301 is applied as a single wrap.

FIG. 4 illustrates a cross-section of a mcVAG and an alternate method of applying a mask using a wrapping fiber according to one embodiment of the present invention. The masking wrap 301 is wrapped around the second inner layer component 102 such that it is positioned tightly against itself in order to avoid penetration of the masking wrap 301 by the conjoining layer 103. The materials composing the masking wrap 301 may be selected as described above for the mask 202. In some embodiments, the masking wrap 301 can be a stainless steel foil. In other embodiments, the masking wrap 301 can be a stainless steel wire. In one embodiment, the stainless steel foil can range from about 0.001 inches thick to about 0.020 inches thick, from about 0.002 inches thick to about 0.01 inches thick, from about 0.003 inches thick to about 0.007 inches thick, or any range therein. In another embodiment, the stainless steel wire can range from about 0.001 inches thick to about 0.020 inches thick, from about 0.003 inches thick to about 0.012 inches thick, from about 0.006 inches thick to about 0.010 inches thick, or any range therein.

Figure 5A:
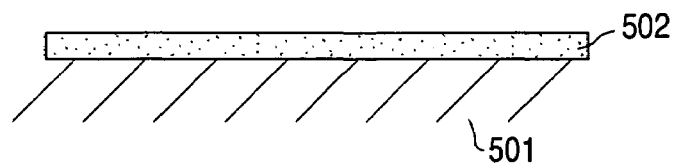
FIGS. 5a-5c illustrate a method of coating a portion of a mcVAG with a fiber-reinforced layer according to one embodiment of the present invention.
Figure 5B:
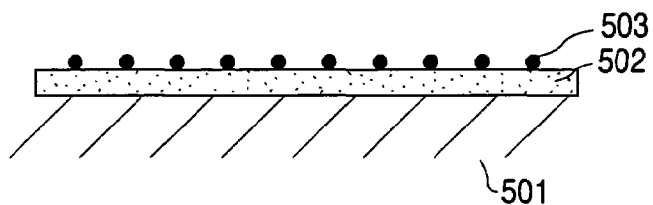
Figure 5C:
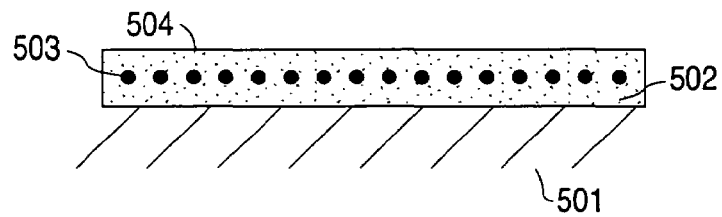

FIGS. 5a-5c illustrate a method of coating a portion of a mcVAG with a fiber-reinforced layer according to one embodiment of the present invention. The fiber-reinforced layer 105 provides enhanced kink resistance. In FIG. 5a, the method of coating comprises applying a foam material 502 to an underlying material 501 such as, for example, the conjoining layer 103. In FIG. 5b, the method further comprises placing a fiber layer 503 on the foam layer 502. In FIG. 5c, the method further comprises applying an additional foam layer 504 on the fiber layer 503 to form a mcVAG with a fiber reinforced layer. The foam layers 502, 504 can be applied using any method of forming a layer described herein and known to one of skill in the art. The fiber layer 503 can be wrapped onto the foam layer 502; preformed and slipped onto the foam layer 502; preformed and crimped onto the foam layer 502; or applied by any method known to one of skill in the art. The steps of applying the foam layer 502, placing a fiber layer 503 and applying an additional foam layer 504 can be repeated to form additional layers of fiber and foam for a stronger fiber-reinforced layer 105 with an even greater kink resistance. It should be appreciated that the fiber-reinforced layer may be formed from a non-foam material.

The conjoining layer 103 and the fiber-reinforced layer 110 can be independently formed from the same or different materials. Examples of materials that may be used to form the conjoining layer 103 and the fiber-reinforced layer 105 include, but are not limited to, silicones; silicone rubbers; synthetic rubbers; polyethers; polyesters; polyolefins; modified polyolefins such as, for example, halogenated polyolefins that include, but are not limited to, fluorinated polyolefins; polyamides; FEP; PFA; polyurethanes; segmented-polyurethanes; segmented polyether-polyurethanes; polyurethaneurea; silicone-polyurethane copolymers; and, any analogs, homologues, congeners, derivatives, salts and combinations thereof. In one embodiment, the conjoining layer 103 and the fiber-reinforced layer 105 may be independently comprised of polyurethane. In another embodiment, the conjoining layer 103 and the fiber-reinforced layer 105 may be independently comprised of Thoralon®.

In some embodiments, the conjoining layer 103 and the fiber-reinforced layer 105 may also include a gel. Examples of gels that may be used in the present invention include, but are not limited to, gelatin, collagen, albumin, casein, algin, carboxy methyl cellulose, carageenan, furcellaran, agarose, guar, locust bean gum, gum arabic, hydroxyethyl cellulose, hydroxypropyl cellulose, methyl cellulose, hydroxyalkylmethyl cellulose, pectin, partially deacetylated chitosan, starch and starch derivatives, including amylose and amylopectin, xanthan, polylysine, hyaluronic acid, heparin and any analogs, homologues, congeners, derivatives, salts and combinations thereof. In some embodiments, the gel can be a hydrogel.

The fiber layer 503 can be comprised of any material suitable for incorporation into a layer that is designed to provide kink-resistance to the mcVAG. Examples of suitable materials for use in the fiber layer 503 include, but are not limited to, metals, alloys, polymers and combinations thereof. Examples of metals and metal alloys include, but are not limited to, ELASTINITE® (Guidant Corp.), NITINOL (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies), and combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Examples of polymers include, but are not limited to, segmented-polyurethanes and other segmented or block copolymers with similar structural properties. Examples of segmented-polyurethanes include, but are not limited to, polyether urethane ureas, polyether urethanes and polyester urethanes. While segmented polyurethanes are highly effective base polymers for use in the present invention, other segmented or block copolymers with similar structural properties may also be used. Examples of other segmented or block copolymers include, but are not limited to, polyester-polyethers, polyesters, polyether-polyamides, polyamides (e.g. nylon), styrene-isoprenes, styrene butadienes, thermoplastic polyolefins, styrene-saturated olefins, polyester-polyester, ethylene-vinyl acetate, ethylene-ethyl acrylate, ionomers, thermoplastic polydienes. Reinforced rubbers may be used where the reinforcement serves the same purpose as the hard block in the segmented copolymer. In one embodiment, the fiber material comprises a polyester such as, for example, Dacron® (EI du Pont de Nemours and Co., Inc.) or Hytrel® (EI du Pont de Nemours and Co., Inc.). In another embodiment, the fiber comprises a polyamide and, preferably, the polyamide is Nylon® (EI du Pont de Nemours and Co., Inc.) In another embodiment, the fiber material comprises a metal or metal alloy. In one example, the fiber is low-ferromagnetic. In another example, the fiber is non-ferromagnetic. In another example, the fiber comprises stainless steel.

In one embodiment, the tensile strength of the fiber material should be in the range of from about 2500 psi to about 2,500,000 psi, from about 10,000 psi to about 2,500,000 psi, from about 50,000 psi to about 100,000 psi, or any range therein. In some embodiments, a wound fiber layer can have a pitch in the range of from about 1 to about 10, from about 1.5 to about 7.5, from about 2 to about 6, or any range therein. "Pitch" is a measure of the ratio of the distance between the spiral loops to diameter of the fiber.

Figure 6A:
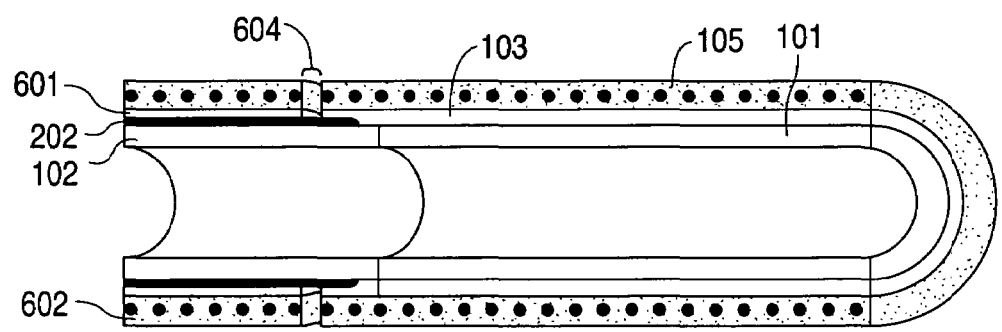
FIGS. 6a and 6b illustrate the removal of a mask and overlying materials according to one embodiment of the present invention.
Figure 6B:
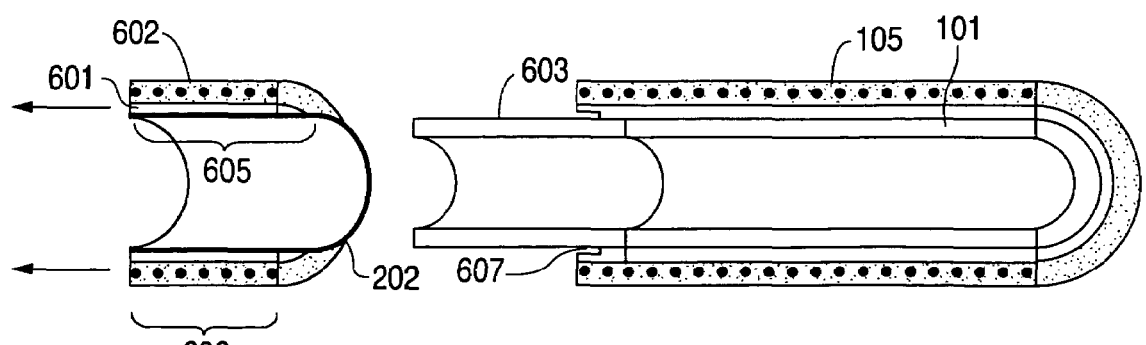

FIGS. 6a and 6b illustrate the removal of a mask and overlying materials according to one embodiment of the present invention. The mask 202 and any overlying materials such as, for example, a portion 601 of the conjoining layer 103 and a portion 602 of the fiber-reinforced layer 105, are removed to expose an underlying bare portion 603 of the second inner layer component 102. In one embodiment, the underlying bare portion 603 can be ePTFE. In one embodiment, there is only one second inner layer component 102. In another embodiment, there is a second inner layer component 102 at each end of the mcVAG, and the lengths of the second inner layer components are not equal.

In FIG. 6a, removing the mask comprises making a circumferential cut 604 to a depth of the outermost surface of the mask 202 and through any overlying materials 601, 602 at a position such that the length 605 of the mask 202 exceeds the length 606 of the overlying materials 601, 602. In FIG. 6b, the mask 202 and overlying materials 601, 602 are removed to create an overhang 607. The overhang 607 defines a circumferential space between the conjoining layer 103 and the second inner layer 102 and covers rough edges that may be created from removing the mask 202 and the overlying materials 601, 602 from the mcVAG. It is to be appreciated that the overhang 607 is optional. In some embodiments, there is no overhang 607. In other embodiments, the overhang 607 is minimized. In one embodiment, the overhang 607 ranges from about 0.01 inches to about 0.25 inches in length, from about 0.03 inches to about 0.20 inches in length, from about 0.05 inches to about 0.15 inches in length, from about 0.07 inches to about 0.12 inches in length, or any range therein.

Figure 7A:
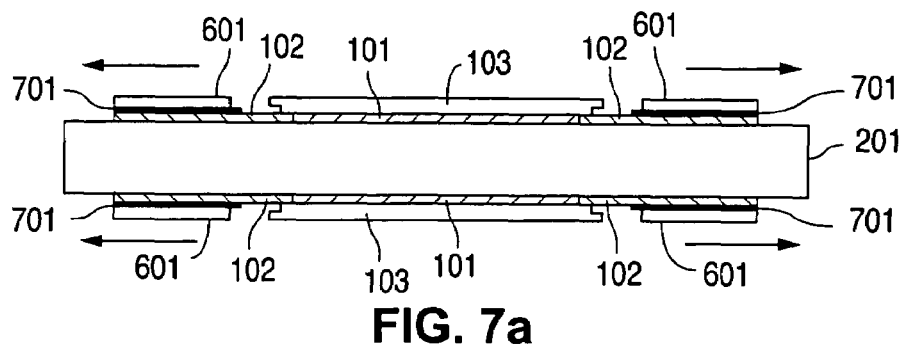
FIGS. 7a and 7b illustrate a layered mask system according to one embodiment of the present invention.
Figure 7B:
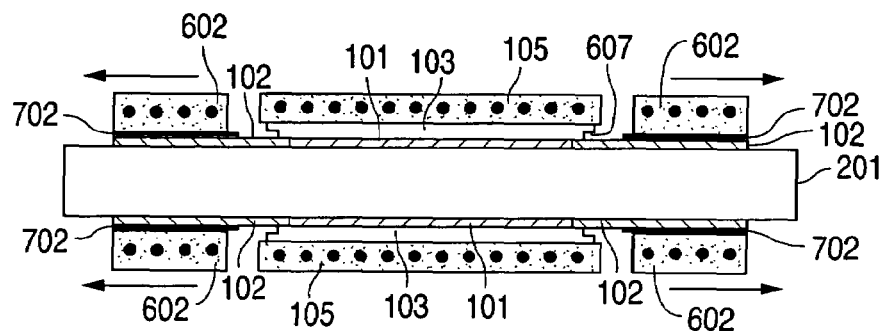

FIGS. 7a and 7b illustrate a layered mask system according to one embodiment of the present invention. In some embodiments, the use of a single mask 202 can increase the diameter of a mcVAG during its formation to a size greater than the orifice needed in a next dipping step of the formation process. Accordingly, a system that avoids such a diametrical constraint would be beneficial. In FIG. 7a, a first mask 701 is removed with overlying material 601 as described above in FIG. 6 after depositing the conjoining layer 103. In FIG. 7b, a second mask 702 is applied to the second inner layer component 102. A coating of a fiber-reinforced layer 105 is then applied to the second mask 702 and the conjoining layer 103. The second mask 702 is removed with overlying material 602 as described above in FIG. 6 after depositing the fiber-reinforced layer 105 to produce a mcVAG with a fiber-reinforced layer and an overhang 607, as described above. Each mask used in the layered masking system is removed with overlying layers formed during construction of the mcVAG and replaced by another mask when necessary to prevent an excessive buildup of layers that would otherwise increase the diameter of the mcVAG to a size greater than the next size orifice used in the dipping process.

It should be appreciated that a mask 202 may not have to be in direct contact with the composite inner layer 102, 101, 102 in coating applications that are precise. For example, in some embodiments using spray coating methods, the mask can be placed between the composite inner layer 102, 101, 102 and the source of the spray. Furthermore, when a spray is sufficiently precise, a mask 202 may be unnecessary to maintain bare portion 603 during formation of each of the layers in the mcVAG.

Figure 8A:
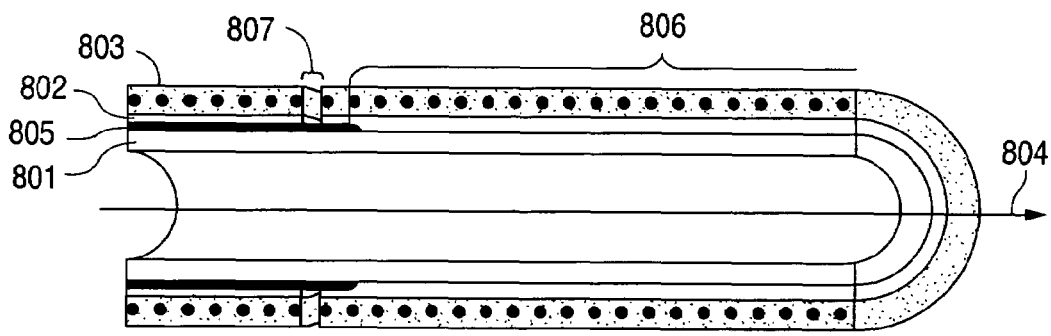
FIGS. 8a and 8b illustrate a cross-section of a mcVAG according to one embodiment of the present invention.
Figure 8B:
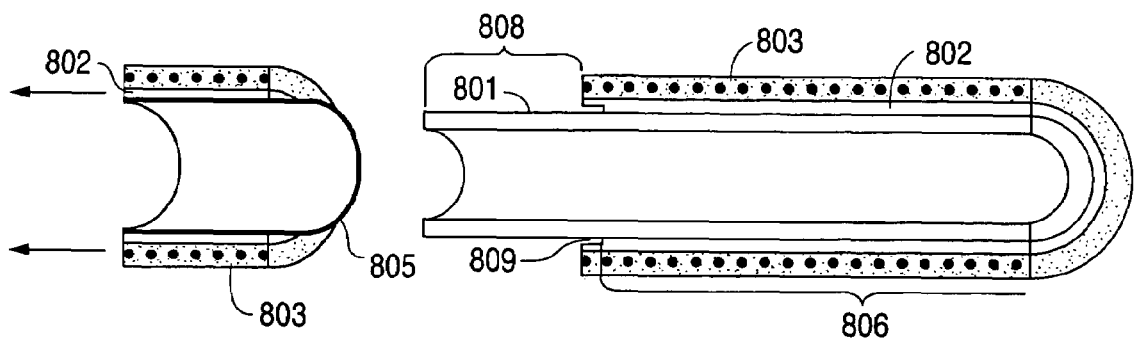

FIGS. 8a and 8b illustrate a cross-section of a mcVAG according to one embodiment of the present invention. In FIG. 8a, a mcVAG having a single inner layer comprises a first layer 801, a second layer 802, and a fiber-reinforced layer 803. The method of constructing a mcVAG with a single inner layer comprises depositing the second layer 802 on a central portion 806 of the first layer 801 and coating the second layer 802 with the fiber-reinforced layer 803 to complete construction of a multilayer composite vascular access graft. Methods of forming the layers and optional methods for applying and removing a mask 805 are described above and generally comprise making a circumferential cut 807 through overlying materials 802, 803. In FIG. 8b, the mask 805 and overlying materials 802, 803 are removed to expose a portion 808 of first layer 801 with a slight overhang 809. It should be appreciated that the mcVAG can be comprised of any number of layers and that each layer of the mcVAG can be formed by any method known to one of skill in the art. Each layer of the present invention can be porous or non-porous. In one embodiment, the bare portion 808 is only at one end of the mcVAG. In another embodiment, there is a bare portion 808 at each of the mcVAG, and the lengths of the bare portions 808 are not equal.

Examples of materials that may be used to form the first layer 801 include, but are not limited to, silicones; silicone rubbers; synthetic rubbers; polyethers; polyesters; polyolefins; modified polyolefins such as, for example, halogenated polyolefins that include, but are not limited to, fluorinated polyolefins; polyamides; FEP; PFA; polyurethanes; segmented-polyurethanes; segmented polyether-polyurethanes; polyurethaneurea; silicone-polyurethane copolymers; and, any analogs, homologues, congeners, derivatives, salts and combinations thereof. In one embodiment, the first layer 801 can be comprised of PTFE. In another embodiment, the first layer 801 can be comprised of ePTFE. In another embodiment, the first layer 801 can be porous, and the porous structure of the first can be obtained by the methods described above.

Examples of materials that may be used to form the second layer 802 or the fiber-reinforced layer 803 include, but are not limited to, silicones; silicone rubbers; synthetic rubbers; polyethers; polyesters; polyolefins; modified polyolefins such as, for example, halogenated polyolefins that include, but are not limited to, fluorinated polyolefins; polyamides; FEP; PFA; polyurethanes; segmented-polyurethanes; segmented polyether-polyurethanes; polyurethaneurea; silicone-polyurethane copolymers; and, any analogs, homologues, congeners, derivatives, salts and combinations thereof. In one embodiment, the second layer 802 or the fiber-reinforced layer 803 can be comprised of polyurethane. In another embodiment, the second layer 802 or the fiber-reinforced layer 803 can be comprised of Thoralon®. In another embodiment, the second layer 802 or the fiber-reinforced layer 803 can be comprised of a gel, and examples of gels are described above.

The inner lumen 804 can be designed to promote endothelialization for prevention or inhibition of thrombus formation. As described above, inner lumen 804 can be porous or rough to promote endothelialization; at least partially coated with an antiplatelet, anticoagulant, antifibrin, antithrombin to prevent or inhibit thrombus formation; and treated in other ways to prevent or inhibit thrombus formation. Other ways to treat inner lumen 804 include, but are not limited to, designing the inner lumen 804 to act as a scaffolding for host cells that secrete polypeptides that are antithrombogenic and modifying the surface of the inner lumen 804 with, for example, polyethylene glycol.

While particular embodiments of the present invention have been shown and described, it will be obvious to those skilled in the art that changes and modifications can be made without departing from this invention in its broader aspects.

I claim:

1. A multilayer composite vascular access graft comprising a first layer;
   a second layer, wherein an edge of the second layer is in contact with or positioned at a distance from an edge of the first layer to form a single horizontally aligned composite layer; and
   a conjoining layer disposed outside of and on the composite layer to conjoin the first layer to the second layer.

2. A multilayer composite vascular access graft comprising
   a first layer;
   a second layer in contact with or positioned at a distance from the first layer to form a horizontally aligned composite layer; and a conjoining layer disposed outside of and on the composite layer to conjoin the first layer to the second layer within a multilayer composite vascular access graft; and
   a fiber-reinforced layer disposed outside of and on the conjoining layer.

3. The multilayer composite vascular access graft of claim 2, wherein the fiber-reinforced layer comprises a material selected from the group consisting of silicones; silicone rubbers; synthetic rubbers; polyethers; polyesters; polyolefins; modified polyolefins; polyamides; FEP; PFA; polyurethanes; segmented-polyurethanes; segmented polyether-polyurethanes; polyurethaneurea; silicone-polyurethane copolymers; and, any analogs, homologues, congeners, derivatives, salts and combinations thereof.

4. The multilayer composite vascular access graft of claim 2, wherein the fiber-reinforced layer comprises a material selected from a group consisting of polyurethane, polyester, BPS-215 polyurethaneurea, modifying additives and BPS-215 polyurethaneurea.

5. The multilayer composite vascular access graft of claim 1, wherein the conjoining layer covers the first layer and a segment of the second layer such that a portion of the second inner layer is exposed.

6. The multilayer composite vascular access graft of claim 3, wherein the conjoining layer includes an overhang portion disposed over the second layer.

7. The multilayer composite vascular access graft of claim 1, wherein the first layer is porous.

8. The multilayer composite vascular access graft of claim 1, wherein the first layer comprises a material selected from the group consisting of silicones; silicone rubbers; synthetic rubbers; polyethers; polyesters; polyolefins; modified polyolefins; polyamides; fluorinated ethylene propylene copolymer (FEP); polyfluorinated alkanoate (PFA); polyurethanes; segmented-polyurethanes; segmented polyether-polyurethanes; polyurethaneurea; silicone-polyurethane copolymers; and, any analogs, homologues, congeners, derivatives, salts and combinations thereof.

9. The multilayer composite vascular access graft of claim 1, wherein the first layer comprises polyurethane.

10. The multilayer composite vascular access graft of claim 1, wherein the first layer comprises BPS-215 polyurethaneurea or modifying additives and BPS-215 polyurethaneurea.

11. The multilayer composite vascular access graft of claim 1, wherein the second layer comprises expanded polytetrafluoroethylene (ePTFE).

12. The multilayer composite vascular access graft of claim 1, wherein the conjoining layer is non-porous.

13. The multilayer composite vascular access graft of claim 1, wherein the conjoining layer comprises a material selected from the group consisting of silicones; silicone rubbers; synthetic rubbers; polyethers; polyesters; polyolefins; modified polyolefins; polyamides; FEP; PFA; polyurethanes; segmented-polyurethanes; segmented polyether-polyurethanes; polyurethaneurea; silicone-polyurethane copolymers; and, any analogs, homologues, congeners, derivatives, salts and combinations thereof.

14. The multilayer composite vascular access graft of claim 1, wherein the conjoining layer comprises polyurethane.

15. The multilayer composite vascular access graft of claim 1, wherein the conjoining layer comprises polyurethaneurea or modifying additives and BPS-215 polyurethaneurea.

16. The multilayer composite vascular access graft of claim 1, wherein the conjoining layer comprises a gel.

17. The multilayer composite vascular access graft of claim 1, wherein the multilayer composite vascular access graft is at least partially coated with an antithrombin agent.

18. A multilayer composite vascular access graft comprising a first layer, a separate second layer and a separate fiber-reinforced layer, wherein the second layer is deposited outside of and on the first layer, and the outside of the second layer is coated with the fiber-reinforced layer.

19. The multilayer composite vascular access graft of claim 18, wherein the second layer covers only a segment of the first layer, and the second layer includes an overhang so as to provide a circumferential space between the overhang and the first layer.

* * * * *